(12) United States Patent
Sato et al.

(10) Patent No.: US 9,522,109 B2
(45) Date of Patent: Dec. 20, 2016

(54) SKIN COLLAGEN ENHANCING AGENT

(71) Applicant: J-Oil Mills, Inc., Tokyo (JP)

(72) Inventors: Toshiro Sato, Tokyo (JP); Rumi Kawahara, Tokyo (JP); Shuichi Kamo, Tokyo (JP)

(73) Assignee: J-Oil Mills, Inc., Tokyo (JP)

( * ) Notice: Subject to any disclaimer, the term of this patent is extended or adjusted under 35 U.S.C. 154(b) by 0 days.

(21) Appl. No.: 14/623,243

(22) Filed: Feb. 16, 2015

(65) Prior Publication Data

US 2015/0164767 A1 Jun. 18, 2015

Related U.S. Application Data

(60) Division of application No. 13/644,210, filed on Oct. 3, 2012, now abandoned, which is a continuation of application No. PCT/JP2011/068123, filed on Aug. 9, 2011.

(30) Foreign Application Priority Data

Feb. 14, 2011 (JP) .................. 2011-028189

(51) Int. Cl.
| | | |
|---|---|---|
| *A61K 8/67* | (2006.01) | |
| *A61K 31/122* | (2006.01) | |
| *A61Q 19/08* | (2006.01) | |
| *A61K 8/35* | (2006.01) | |
| *A61K 45/06* | (2006.01) | |
| *A61K 8/65* | (2006.01) | |

(52) U.S. Cl.
CPC ............... *A61K 8/67* (2013.01); *A61K 8/355* (2013.01); *A61K 8/65* (2013.01); *A61K 31/122* (2013.01); *A61K 45/06* (2013.01); *A61Q 19/08* (2013.01); *A61K 2800/40* (2013.01)

(58) Field of Classification Search
CPC ...... A61K 31/122; A61K 8/355; A61K 45/06; A61K 2800/40; A61K 8/65; A61K 8/67; A61Q 19/08
See application file for complete search history.

(56) References Cited

U.S. PATENT DOCUMENTS

| | | | |
|---|---|---|---|
| 2004/0234560 A1 | 11/2004 | Kimura et al. | |
| 2005/0123603 A1* | 6/2005 | Dalland | A23L 1/30 424/456 |
| 2009/0234022 A1 | 9/2009 | Salentine et al. | |
| 2009/0239952 A1 | 9/2009 | Perez-Soler et al. | |
| 2010/0099918 A1 | 4/2010 | Sato et al. | |
| 2010/0130618 A1* | 5/2010 | Vaidya | A61K 31/122 514/681 |

FOREIGN PATENT DOCUMENTS

| | | |
|---|---|---|
| JP | 1135455 A | 5/1989 |
| JP | 5320039 A | 12/1993 |
| JP | 10007541 A | 1/1998 |
| JP | 2004196759 A | 7/2004 |
| JP | 200791637 A | 4/2007 |
| JP | 2007186471 A | 7/2007 |
| JP | 200894750 A | 4/2008 |
| JP | 2008133270 A | 6/2008 |
| JP | 2008189607 A | 8/2008 |
| JP | 2008260747 A | 10/2008 |
| JP | 2008280296 A | 11/2008 |
| JP | 2009184997 A | 8/2009 |
| JP | 2009249366 A | 10/2009 |
| JP | 2009298724 A | 12/2009 |
| JP | 201095499 A | 4/2010 |
| JP | 2010215648 A | 9/2010 |
| WO | 2009063485 A2 | 5/2009 |

OTHER PUBLICATIONS

Machine translation of JP 5320039 A, pp. 1-5, accessed Jun. 25, 2013.*
Menaquinone-7, from https://pubchem.ncbi.nlm.nih.gov/compound/Menaquinone_7, p. 1, accessed Feb. 12, 2016.*
Definition of percutaneous, from http://medical-dictionary.thefreedictionary.com/percutaneous, pp. 1-3, accessed Feb. 12, 2016.*
Mills, Pharmaceutical excipients—an overview including considerations for paediatric dosing, pp. 1-44, Jun. 2010.*
International Search Report received in corresponding PCT/JP2011/068123 dated Nov. 15, 2011.
Y. Ide et al., "Inhibition of Matrix Metalloproteinase Expression by Menatetrenone, a Vitamin K2 Analogue", Oncol. Rep. 2009, vol. 22, (pp. 599-604).
M. Bond, et al., "Nuclear Factor kB Activity is Essential for Matrix Met Alloproteinase-1 and -3 Upregulation in Rabbit Dermal Fibroblast", Biochem. Biophys. Res. Commun., 1999, vol. 264, (pp. 561-567).
M. Elson, MD, "Topical Phytonadione (Vitamin K1) in the Treatment of Actinic and Traumatic Purpura", vol. 8, No. 12, Dec. 1995, Cosmetic Dermotology (pp. 25-27).
M. Elson, MD, et al., "Treatment of Periorbital Hyperpigmentation with Topical Vitamin K/Vitamin A", Cosmetic Dermotology, Dec. 1999 (pp. 32-34).
T. Ichikawa, et al., "The Journal of Biological Chemistry", ASBMB, vol. 281, No. 25, Jun. 23, 2006, (pp. 16927-16934).
T. Ichikawa, et al., "Vitamin K2 Induces Phosphorylation of Protein Kinase A and Expression of Novel Target Genes in Osteoblastic Cells", Journal of Molecular Endocrinology, 2007, (pp. 239-247).

(Continued)

*Primary Examiner* — Julie Ha
*Assistant Examiner* — Li Ni Komatsu
(74) *Attorney, Agent, or Firm* — Edell, Shapiro & Finnan, LLC

(57) ABSTRACT

A method for enhancing skin collagen in an individual includes administering a composition to the individual, the composition comprising a skin collagen enhancing agent comprising menaquinone-7 as an active ingredient. In addition, a composition is provided in the form of at least one of an emulsion and a cream, the composition including a skin collagen enhancing agent comprising menaquinone-7 as an active ingredient.

5 Claims, 1 Drawing Sheet

(56) References Cited

OTHER PUBLICATIONS

Rite et al., UV-light-induced signal cascades and skin aging, Ageing Research Reviews, 2002, 1, pp. 705-720.
Nature Made Vitamin K2, from www.naturemade.com/products/health-solutions/vitamin-k2, pp. 1-2, accessed Apr. 11, 2014.
Collagen—*Homo sapiens*, from http:/www.ncbi.nlm.nih.gov/protein/BAA04809.1, pp. 1-2, accessed Apr. 11, 2014.
Kincl et al., Sustained Release Preparations, XVI: Collagen as a Drug Carrier, Arch. Pharm. (Weinheim), 1984, 317, pp. 657-661.
Definition of derivative, from http:/cancerweb.ncl.ac.uk/cgi-bin/omd?query=derivative, pp. 1-5, accessed Jul. 7, 2005.
Bernstein et al, Glycolic acid treatment increases type I collagen mRNA and hyaluroniic acid content of human skin, Dermatol. Surg. 2001, 27, pp. 429-433.

* cited by examiner

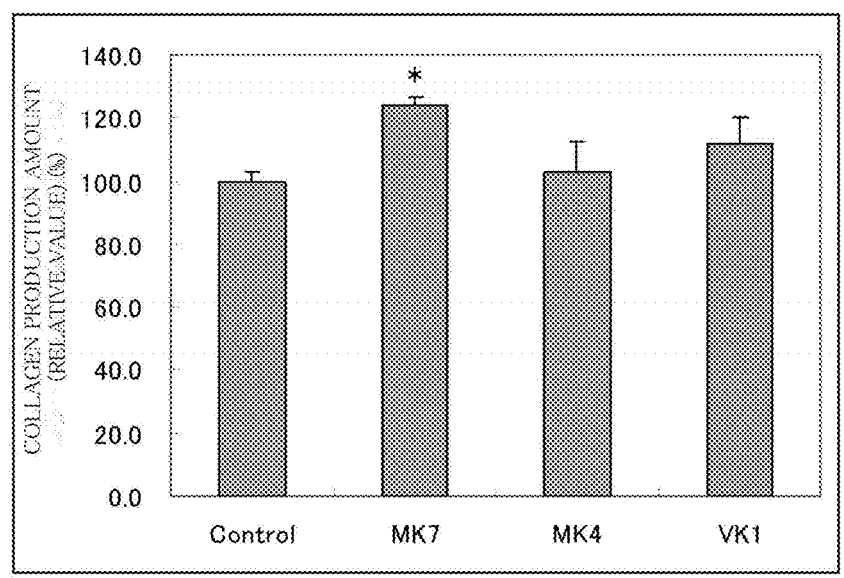

SKIN COLLAGEN ENHANCING AGENT

CROSS REFERENCE TO RELATED APPLICATIONS

This application is a divisional of U.S. patent application Ser. No. 13/644,210, filed Oct. 3, 2012, and entitled "Skin Collagen Enhancing Agent", which is a continuation of PCT/JP2011/068123, filed Aug. 9, 2011, and entitled "Skin Collagen Enhancing Agent", which claims priority from Japanese Patent Application No. 2011-028189, filed Feb. 14, 2011. The entire contents of these applications are hereby incorporated by reference in their entireties.

TECHNICAL FIELD

The present invention relates to a skin collagen enhancing agent that is effective for improvement and/or prevention of skin disease, allergy, and aging, and more specifically relates to a highly safe skin collagen enhancing agent derived from foodstuffs.

BACKGROUND

The skin mainly consists of the epidermis, the dermis, and the subcutaneous tissue. The dermis is located beneath the epidermis for supporting the skin structure and is filled with a biological structure, called an extracellular matrix, constituted of, for example, collagen and hyaluronic acid. The extracellular matrix components are produced by, for example, fibroblasts. In the healthy youthful skin, production of the extracellular matrix components such as collagen is satisfactory for preventing infection by bacteria or viruses, skin disease, and entrance of foreign matter such as allergen and maintaining skin elasticity and moisture. It is said that aging of the skin represented by symptoms such as a spot, wrinkles, sagging, and rough skin progresses with a decrease in extracellular matrix components such as collagen.

There are many reports on materials that increase skin collagen. In most of these materials, however, the effects are insufficient, the manufacturing costs are very high, and they have problems in, for example, safety because of insufficient experience of eating them.

Vitamin K is generally a vitamin necessary for converting specific glutamate residues in vitamin K-dependent proteins into γ carboxyglutamic acid (Gla). Examples of the vitamin K-dependent protein include some factors related to blood coagulation produced in the liver, osteocalcin produced in the bone tissue, and matrix Gla protein produced in the soft tissue such as blood vessels.

Effects of vitamin K on the skin, prevention and curing skin conditions related to inflammation due to anti-EGFR therapy and rashes are known. In addition, vitamin K can cure skin disease related to skin pigmentation, such as melanin and shows advantageous effects against bruising or dark circles under the eyes. A combination formulation of vitamin K and vitamin E that improves symptoms such as freckles of the face, dark circles under the eyes, redness, and hot flushes, and a combination with, for example, lipoic acid is known as an external preparation for skin.

One type of vitamin K2, menaquinone-4, is known to have an effect of increasing the collagen in osteoblasts through an SXR receptor. Menaquinone-4 is also known to act on factors working in protein kinase A-dependent pathways.

Conventionally known materials that promote production of skin collagen do not necessarily satisfy effectiveness and safety. Accordingly, it would be desirable to provide a material that is a food ingredient or nutrient with safety and experience having been eaten for a long time and that shows a collagen enhancing activity in a small amount.

SUMMARY

In accordance with example embodiments of the present invention, a skin collagen enhancing agent comprises menaquinone-7 as an active ingredient.

In accordance with the present invention, the physiological functions of menaquinone-7, one of vitamin K, which has been supplied as dietary intake for a long time, have been extensively studied. Among the functions, the effects on skin cells have been studied and, as a result, a surprising determination has been made that menaquinone-7 only has an activity of promoting production of collagen in skin cells and that menaquinone-4 does not have such an activity.

Though functions of vitamin Ks on the skin are known, as shown in Examples and Comparative Examples described below, it has not been known that menaquinone-4 does not have a skin collagen enhancing activity and that menaquinone-7 has a collagen enhancing activity. It is not expected at all that a skin collagen enhancing agent containing menaquinone-7 as an active ingredient can be provided by the present invention.

Furthermore, the present inventors have found that orally administered menaquinone-7 reaches the level of an effective dose at the skin. Based on this finding, the present invention also provides a percutaneously administrative agent and an orally administrative agent each containing the skin collagen enhancing agent. It was not obvious that conventionally known skin collagen promoting compounds are delivered to the skin when orally administered. By summing up with the fact that menaquinone-4 does not have a skin collagen enhancing activity, it is totally unexpected that a percutaneously administrative agent and an orally administrative agent containing the skin collagen enhancing agent of which active ingredient is menaquinone-7 have a skin collagen-increasing activity.

The collagen enhancing agent containing menaquinone-7 as an active ingredient of the present invention is significantly effective for, for example, preventing infection by bacteria or viruses, skin disease, and entrance of foreign matter such as allergen; preventing and improving skin aging and wrinkles; and retaining moisture.

An adequate amount of vitamin K required per person per day is 55 to 80 μg (Dietary Reference Intakes for Japanese, 2010), but allowable upper limit of intake is not defined. Accordingly, vitamin K can be recognized to be a highly safe material. In particular, menaquinone-7 is further safer based on the long ingestion experience from natto. Consequently, the collagen enhancing agent of the present invention is excellent in safety compared with conventionally known products as agents for improving or preventing skin wrinkles or for improving or preventing skin aging.

Menaquinone-7 is lipophilic and therefore tends to accumulate in the body compared with conventional collagen enhancing agents. Consequently, menaquinone-7 also has an effect of lasting the activity for a long time. In addition, menaquinone-7 is not catabolized even in oral administration to maintain the function as menaquinone-7 and is therefore a very advantageous collagen enhancing agent.

The collagen enhancing agent of the present invention can be used as a drug and also can be considerably easily administered or used routinely as a supplement or a cosmetic. Accordingly, the collagen enhancing agent can further be used to prevent skin aging and disease.

BRIEF DESCRIPTION OF DRAWINGS

FIG. 1 shows the evaluation results of collagen enhancing activity of menaquinone-7 (MK-7), menaquinone-4 (MK-4), and vitamin K1 (VK1) on normal human dermal fibroblasts, where the amounts of produced collagens are shown as relative values with respect to the amount of collagen, defined as 100, produced per unit amount of protein when no sample is added, and where only menaquinone-7 significantly increased the production amount of collagen.

DETAILED DESCRIPTION OF EMBODIMENTS

An example embodiment of the collagen enhancing agent of the present invention will now be described in detail. Menaquinone-7 that can be used in the skin collagen enhancing agent of the present invention is one type of vitamin K2. Vitamin K2 is classified into from menaquinone-4 to MK-15 depending on the difference in length of isoprenoid side chain. The skin collagen enhancing agent of the present invention contains vitamin K2 of which the isoprenoid side chain has a length of seven as an essential component.

Menaquinone-7 which is largely contained as a nutrient in a foodstuff can be obtained from Fermented soybean called Natto. It is also obtained from fermentation of Bacteria such as *Bacillus subtilis* or lactic acid bacteria. In addition, menaquinone-7 may be chemically synthesized.

The content of menaquinone-7 in the skin collagen enhancing agent of the present invention varies depending on the formulation and administration amount of the composition, but is usually in the range of 0.00002 to 100% by weight, preferably 0.0003 to 70% by weight, and more preferably 0.003 to 50% by weight. A content of menaquinone-7 of 0.00002% by weight or less may be insufficient for administering an amount necessary to obtain a skin collagen-increasing effect.

The skin collagen enhancing agent of the present invention may contain one or more food ingredients conventionally known to have a skin collagen enhancing effect, in addition to menaquinone-7 as an essential component. Alternatively, the skin collagen enhancing agent may also contain a component such as collagen, a collagen degradation product, or a source of collagen, e.g., amino acids.

In the case of using the skin collagen enhancing agent of the present invention as a drug, the drug may contain those usually used as auxiliaries for drugs, in addition to menaquinone-7 as an essential component and optional collagen-producing materials, collagen, collagen degradation products, and amino acids. For example, according to the formulation and route of administration, the drug may contain general-purpose additives, such as an excipient, a disintegrator, a binder, a lubricant, a vitamin, a xanthine derivative, a pH adjuster, a cooling agent, a suspending agent, a thickener, a solubilizing agent, an antioxidant, a coating agent, a plasticizer, a surfactant, water, alcohols, a water-soluble polymer, a sweetener, a flavoring substance, an acidifier, a flavoring agent, and a coloring agent, in the qualitative and quantitative ranges that do not impair the effects of the present invention.

The skin collagen enhancing agent of the present invention is, in order to be used as a drug, formulated into an orally administrative agent, for example, a solid preparation such as a powder, granules, a capsule, a pill, a tablet, a chewable tablet, or a drop, or a liquid preparation such as a drinkable preparation, a liquid agent, a suspension, an emulsion, a syrup, or a dry syrup; or a percutaneously administrative agent such as a solution agent, a liquid agent, an emulsion, or a cream.

In the case of using the skin collagen enhancing agent of the present invention as a drug, the administration route is not particularly limited. For example, oral administration, percutaneous administration, transfusion, or injection (intramuscular, intraperitoneal, subcutaneous, or venous) is employed. Oral administration, such as tablets and capsules, imposes less burden on patients and is therefore preferred.

In the case of using the skin collagen enhancing agent of the present invention in a drug, the administration amount may be appropriately determined depending on the symptoms. In general, in the case of using as a preventive drug, the administration amount of menaquinone-7 per day may be 10 μg to 100 mg, preferably 20 μg to 100 mg, and more preferably 5 to 50 mg; and in the case of using as a therapeutic drug, the amount per day can be 1 to 150 mg.

In the case of using the skin collagen enhancing agent of the present invention as a cosmetic, the cosmetic may contain those usually used as auxiliaries for cosmetics, in addition to menaquinone-7 as an essential component, and optional skin collagen-producing materials, amino acids serving as sources of collagen, collagen degradation products, collagen, and gelatin. Examples of the auxiliaries include polyhydric alcohols such as ethylene glycol, polyethylene glycol, propylene glycol, 1,3-butylene glycol, 1,4-butylene glycol, dipropylene glycol, glycerine, diglycerine, polyglycerine, pentylene glycol, isoprene glycol, glucose, maltose, fructose, xylitol, sorbitol, maltotriose, and erythritol; lower alcohols such as methanol, ethanol, propyl alcohol, isopropyl alcohol, butyl alcohol, and isobutyl alcohol; higher fatty acids such as oleic acid, isostearic acid, lauric acid, myristic acid, palmitic acid, stearic acid, behenic acid, and undecylenic acid; oils and fats such as olive oil, corn oil, camellia oil, macadamia nut oil, avocado oil, rapeseed oil, sesame oil, castor oil, safflower oil, cottonseed oil, jojoba oil, coconut oil, and palm oil; waxes such as carnauba wax, candelilla wax, bees wax, and lanoline; sugars such as sorbitol, mannitol, glucose, sucrose, lactose, and trehalose; thickeners such as carrageenan, xanthan gum, gelatin, pectin, agarose, alginate, dextrin, methylcellulose, ethylcellulose, hydroxypropylcellulose, hydroxyethylcellulose, carboxymethylcellulose, carboxyvinyl polymer, polyvinyl alcohol, polyvinylpyrrolidone, gum arabic, karaya gum, gum tragacanth, and tamarind gum; antiseptics such as phenoxyethanol, methylparaben, ethylparaben, propylparaben, butylparaben, paraoxybenzoic acid ester, benzoic acid, salicylic acid and its salts, sorbic acid and its salts, dehydroacetic acid and its salts, chlorocresol, and hexachlorophen; nonionic surfactants such as sodium lauroyl sulfate and polyoxyethylene sorbitan monooleate; anionic surfactants such as alkylsulfate salts and sodium n-dodecylbenzenesulfonate; cationic surfactants such as polyoxyethylene dodecyl monomethyl ammonium chloride; steroidal and non-steroidal anti-inflammatory drugs; vitamins such as vitamin A, vitamin D, vitamin E, vitamin F, vitamin Ks (other than menaquinone-7); vitamin derivatives such as pyridoxine dicaprylate, pyridoxine dipalmitate, ascorbyl dipalmitate, ascorbyl monopalmitate, and ascorbyl monostearate; antioxidants such as flavonoid and carotenoid; higher aliphatic hydrocarbons such as squalane, squalene, and liquid paraffin; sphingolipids such as ceramide, cerebroside, and sphingomyelin; sterols such as cholesterol and phytosterol; silicones such as methyl polysiloxane, methyl phenyl polysiloxane, methyl cyclopolysiloxane, octamethyl cyclotetrasiloxane, octamethyl cyclopentasiloxane, decamethyl cyclopentasiloxane, and methyl hydrogen polysiloxane; ultraviolet absorbers such as paraaminobenzoic acid, monoglycerin paraaminobenzoate, methyl anthranilate, homomenthyl N-acetylanthranilate, octyl paramethoxycinnamate, and ethyl-4-isopropylcinnamate; minerals such as bentonite, smectite, beidelite, nontronite, saponite, hectorite, sauconite, and stevensite; inorganic pigments such as red iron oxide, yellow iron oxide, black iron oxide, cobalt oxide, ultramarine pigment, iron blue pigment, titanium oxide, and zinc oxide; coloring agents such as red No. 202, yellow No. 4, blue No. 404; flavors; and perfumed oils.

The skin collagen enhancing agent of the present invention is, in order to be used as a cosmetic, formulated into a percutaneously administrative agent such as a solution agent, a liquid agent, an emulsion, a milky lotion, a cream, or a powder; or an orally administrative agent, for example, a solid preparation such as a powder, granules, a capsule, a pill, a tablet, a chewable tablet, or a drop, or a liquid preparation such as a drinkable preparation, a liquid agent, a suspension, an emulsion, a syrup, or a dry syrup.

In the case of using the skin collagen enhancing agent of the present invention as a cosmetic, the administration route is oral administration or percutaneous administration. From the viewpoint of immediate effect as a cosmetic, percutaneous administration in the form of a liquid agent, an emulsion, a milky lotion, or a cream is preferred.

In the case of using the skin collagen enhancing agent of the present invention as a cosmetic, the administration amount (application amount) of menaquinone-7 per day is preferably 0.001 to 100 mg, more preferably 0.05 to 50 mg.

In the case of using the skin collagen enhancing agent of the present invention as a supplement, the supplement may contain those usually used as additives for supplements, in addition to menaquinone-7 as an essential component and optional other collagen-increasing materials. For example, according to the formulation for oral administration, the supplement may contain general-purpose additives, such as an excipient, a disintegrator, a binder, a lubricant, a vitamin, a xanthine derivative, an amino acid, a pH adjuster, a cooling agent, a suspending agent, a thickener, a solubilizing agent, an antioxidant, a coating agent, a plasticizer, a surfactant, water, alcohols, a water-soluble polymer, a sweetener, a flavoring substance, an acidifier, a flavoring agent, and a coloring agent, in the qualitative and quantitative ranges that do not impair the effects of the present invention.

In order to use the skin collagen enhancing agent of the present invention as a supplement, the agent is processed into orally administrative agent such as a powder, granules, a capsule, a pill, a tablet, a chewable tablet, or a drop differently from common foods.

In the case of using the skin collagen enhancing agent of the present invention in functional foods such as a supplement, in the light of safety, the administration amount of menaquinone-7 per day is preferably 0.01 to 50 mg, more preferably 0.01 to 1 mg.

Composition examples of the skin collagen enhancing agent of the present invention are shown below, but the present invention is not limited to the following composition examples.

Composition Example 1

Tablet

TABLE 1

| Composition | Addition amount (parts by weight) |
|---|---|
| Corn starch | 40 |
| Crystal cellulose | 20 |
| Carboxymethyl cellulose | 10 |
| Menaquinone-7 | 0.1 |
| Lactose | Residual quantity |
| Total | 100 |

Composition Example 2

Capsule

TABLE 2

| Composition | Addition amount (parts by weight) |
|---|---|
| Olive oil | 90 |
| Bees wax | 2 |
| Glycerine | 2 |
| Menaquinone-7 | 0.01 |
| Lactose | Residual quantity |
| Total | 100 |

Composition Example 3

Lotion

TABLE 3

| Composition | Addition amount (parts by weight) |
|---|---|
| Ethanol | 10 |
| Glycerine | 3 |
| Propylene glycol | 3 |
| Menaquinone-7 | 0.001 |
| Flavoring/antiseptic | Proper quantity |
| Purified water | Residual quantity |
| Total | 100 |

Composition Example 4

Cream

TABLE 4

| Composition | Addition amount (parts by weight) |
|---|---|
| Squalane | 10 |
| Glycerine | 10 |
| Liquid paraffin | 5 |
| Cetanol | 3 |
| Stearic acid | 2 |
| Lanoline | 2 |
| Menaquinone-7 | 0.5 |

TABLE 4-continued

| Composition | Addition amount (parts by weight) |
|---|---|
| Flavoring/antiseptic | Proper quantity |
| Purified water | Residual quantity |
| Total | 100 |

EXAMPLES

The present invention will now be described in more detail by examples, but is not limited to the following examples.

Example 1

Skin collagen enhancing activity of menaquinone-7 was compared with those of vitamin K1 and menaquinone-4, using normal human fibroblasts. A menaquinone-7 reagent (Wako Pure Chemical Industries, Ltd.) was used after purity validation by HPLC. The comparison was performed at a setting concentration of $1.5 \times 10^{-5}$ M, which is a maximum solubility of vitamin Ks in a cell culture system. Vitamin K1 (Wako Pure Chemical Industries, Ltd.) and menaquinone-4 (Sigma) were used after purity validation by HPLC.

1. Testing Method

Normal human dermal fibroblasts (manufactured by Kurabo Industries Ltd.) were inoculated on a 96-well microplate at a cell density of $2.0 \times 10^4$ cells per well using a Dulbecco's modified Eagle's medium (DMEM) (Sigma) containing 0.5% by weight of fetal bovine serum (FBS). The medium was replaced, 48 hours after the inoculation, by DMEM containing 0.5% by weight of FBS and menaquinone-7 in a concentration shown in Table 5. A test maximum concentration solution was prepared by dissolving menaquinone-7 in ethanol and diluting it 100 times with a DMEM containing 0.5% FBS. The testing method was confirmed to be valid using magnesium ascorbic acid phosphate (VC-PMg) as a positive control. The medium containing a sample was cultured for 48 hours, and the medium supernatant was collected and subjected to ELISA for measuring the amount of type I collagen. The cells were lysed in a 0.5% Triton X-100 solution, and the protein amount was measured.

2. Measurement of Collagen Amount

A medium and a type I collagen solution for a standard curve were placed on each well of a high-absorption ELISA plate, and coating at 37° C. for 2 hours was performed, followed by blocking with a 1% bovine serum albumin (BSA) solution at 37° C. for 1 hour. Primary antibody reaction was performed using anti-human collagen type I antibody (rabbit) diluted with a 0.3% BSA solution at 37° C. for 1 hour. Secondary antibody reaction was performed using Histofine® MAX-PO (rabbit) diluted with a phosphate buffer at 37° C. for 1 hour. A phosphate-citrate buffer (0.1 M, pH 4.0) solution containing 0.3 mg/mL of 2,2'-azinobis(3-ethylbenzothiazoline-6-sulfonic acid)diammonium salt (ABTS) and 0.03% hydrogen peroxide was added thereto, followed by reaction for 20 min. The absorbance of the reaction solution was measured at 405 nm with a microplate reader.

The type I collagen amount in the medium was determined from the standard curve prepared by measurement on the same ELISA plate, and the type I collagen amount per unit amount of protein was calculated by dividing the type I collagen amount in the medium by the total protein amount of the cells.

FIG. 1 shows the evaluation results of collagen enhancing activities of menaquinone-7, vitamin K1, and menaquinone-4 (each at a high dose of $1.5 \times 10^{-5}$ M) on normal human dermal fibroblasts as relative values with respect to the amount of type I collagen, defined as 100, produced per unit amount of protein when no sample is added. The test was performed at n=6 for each group containing a sample, and the results are each shown as an average+standard deviation. The statistical processing was performed by a Student t-test against the control group not containing the sample, and the symbol * indicates a significance level of less than 1%.

As shown in FIG. 1, only menaquinone-7 (MK-7 in FIG. 1) significantly increased the production amount of collagen. Menaquinone-4 (MK-4 in FIG. 1) was also evaluated for collagen production at an amount of four times this, i.e., $6.0 \times 10^{-5}$ M, but the production amount of collagen did not increase at all.

Example 2

The collagen enhancing activities of menaquinone-7 for human dermal fibroblasts were investigated in the concentration range shown in Table 5. The results are shown in Table 5. The test of each group containing a sample was performed at n=6, and the results are each shown as an average value. The statistical processing was performed by a Student t-test against the control group not containing the sample, and the symbol * indicates a significance level of less than 1%.

TABLE 5

| Menaquinone-7 concentration (mol) | Type I collagen amount (ng/μg protein) (average ± SD) | t-test |
|---|---|---|
| 0 | 8.91 ± 0.26 | |
| $0.5 \times 10^{-6}$M | 10.66 ± 0.48 | * |
| $1 \times 10^{-6}$M | 10.26 ± 0.44 | * |
| $3 \times 10^{-6}$M | 10.41 ± 0.49 | * |
| $1 \times 10^{-5}$M | 11.03 ± 0.23 | * |

As shown Table 5, it is obvious that menaquinone-7 significantly promotes production of type I collagen of human dermal fibroblasts even at a low concentration of $0.5 \times 10^{-6}$ M.

Example 3

Wistar rats (male, 5-week old) were freely fed with purified feed AIN93G (manufactured by Oriental Yeast) for one week for habituation, and then separated into groups each consisting of three rats so that the total weight of each group was the same. Three rats in each group were freely fed with a rat standard diet (AIN93G) or a menaquinone-7-containing feed (menaquinone-7: 150 μg/g) composed of rat standard diet (AIN93G) and menaquinone-7 for 90 days. Then, vitamin K concentration in the skin was measured. Vitamin K was analyzed by high-performance liquid chromatography with post-column reduction using platinum black and fluorescence detection (Sato, et al., Biochim Biophys. Acta, 1622, 145-150, 2003). The results are shown in Table 6.

TABLE 6

| Feed | MK-7 concentration (ng/g) in skin |
|---|---|
| Standard diet | not detected |
| MK-7-containing diet | 427 ± 243* |

*average ± SD

Menaquinone-7 in a concentration of exceeding a menaquinone-7 amount ($0.5 \times 10^{-6}$ M: 325 ng/g) necessary for promoting collagen production was detected in the skin tissue by feeding 150 μg/g of menaquinone-7 diet. This suggests that oral administration is a promising administration route for menaquinone-7.

Example 4

Four-week old male Crl:CD(SD)(SPF) rats were habituated after arrival till the start of administration, including one week for quarantine. During the quarantine and habituation, general conditions were observed every day, and the weights were measured on the first day (the day following the arrival), the third day, and the seventh day. The rats were separated into four groups each consisting of five rats so that the total weight of each group was the same.

Rats were freely fed for 90 days with any one of three types of menaquinone-7-containing feeds by adding menaquinone-7 to rat standard diet AIN93G: high MK7 diet (menaquinone-7: 45.4 μg/g diet), moderate MK7 diet (menaquinone-7: 15 μg/g diet), and low MK7 diet (menaquinone-7: 4.54 μg/g diet); or MK7-free diet.

The rats were subjected to fasting on the last day and then dissected. The hair at the abdomen region was carefully shaved with hair clippers, and the skin including the derm was sampled. The skin was cut into about 100 mg pieces and they were exactly weighed. The skin collagen amount was measured with a skin collagen measurement kit (trade name: Sircol Collagen Assay Kit, manufactured by Biocolor). Increased amounts of collagen in three groups fed with the diet containing MK7 were compared with that in the group fed with the MK7-free diet as a control. The statistical processing was performed by a Student t-test. A significance level P<0.05 was determined as to have significant difference. Table 7 shows the results. In the table, the symbol * means a significant difference.

TABLE 7

| MK7 amount in feed (μg/g) | Type I collagen amount (μg/mg wet skin weight) (average ± SD) | Rate of increase of collagen* (%) | t-test |
|---|---|---|---|
| 0 | 38.43 ± 4.56 | — | — |
| 4.54 | 40.97 ± 6.69 | 6.6 | — |
| 15.0 | 43.33 ± 2.42 | 12.8 | — |
| 45.4 | 45.18 ± 4.23 | 17.6 | * |

*Rate of increase of collagen = [(type I collagen amount)/(type I collagen amount in MK7-free diet group) − 1] × 100

As shown in Table 7, oral administration of MK7 showed a tendency of dose-dependently increasing the amount of collagen. In addition, administration of MK7 by a 45.4 μg/g diet was confirmed to statistically significantly increase skin collagen.

The invention claimed is:

1. A method for enhancing skin collagen in an individual in need thereof, the method comprising:
   administering percutaneously a composition to the individual, wherein the composition comprises a skin collagen enhancing agent comprising menaquinone-7 as an active ingredient, the composition is in the form of a liquid, and the amount of menaquinone-7 administered to the individual via the composition is from 10 μg to 100 mg per day.

2. The method of claim 1, wherein the composition further comprises at least one of a drug and a supplement, and wherein the at least one of the drug and the supplement further comprises at least one additive selected from the group consisting of an excipient, water, and an alcohol.

3. The method of claim 1, wherein the menaquinone-7 is obtained from at least one of natto fermented soybean, fermentation of bacteria, and chemically synthesized menaquinone-7.

4. The method of claim 1, wherein the individual has skin aging or wrinkles.

5. A method for enhancing skin collagen in an individual in need thereof, the method comprising:
   administering percutaneously a composition to the individual, wherein the composition comprises a skin collagen enhancing agent comprising menaquinone-7 as an active ingredient, and wherein the individual has skin aging or wrinkles.

* * * * *